United States Patent [19]

Meadows

[11] Patent Number: 4,798,600

[45] Date of Patent: Jan. 17, 1989

[54] CONDOM DEVICE AND METHOD FOR USING SAME

[76] Inventor: Michael E. Meadows, 37 James Rd., Hatboro, Pa. 19040

[21] Appl. No.: 61,890

[22] Filed: Jun. 12, 1987

[51] Int. Cl.$^4$ .............................................. A61F 5/44
[52] U.S. Cl. .................................. 604/347; 128/839; 128/844
[58] Field of Search .................. 604/330, 349–353, 604/331, 347; 128/132 R

[56] References Cited

U.S. PATENT DOCUMENTS

| | | | |
|---|---|---|---|
| 899,251 | 9/1908 | Graham | 604/330 |
| 3,520,305 | 7/1970 | Davis | 604/349 |
| 3,536,066 | 10/1970 | Ludwig | 128/132 R |
| 3,661,156 | 5/1972 | McLaughlin | 604/349 |
| 4,664,104 | 5/1987 | Jaicks | 604/353 |

FOREIGN PATENT DOCUMENTS

| | | | |
|---|---|---|---|
| 36015 | 7/1908 | Fed. Rep. of Germany | 604/349 |
| 867582 | 1/1953 | Fed. Rep. of Germany | 604/349 |
| 1122860 | 6/1986 | Japan | 604/349 |

OTHER PUBLICATIONS

"USA Is Testing New Birth Control Device", USA Today, Thursday, Feb. 25, 1988, p. 5D.

*Primary Examiner*—C. Fred Rosenbaum
*Assistant Examiner*—J. L. Kruter
*Attorney, Agent, or Firm*—David J. Johns

[57] ABSTRACT

The present invention discloses an improved condom which provides a high degree of protection against disease and pregnancy, and exceptional stimulation of the penis. The interior walls of the condom are used to directly stimulate the penis. This provides a sensation similar to unprotected sexual intercourse while avoiding the need for thin condom sheath materials which can compromise the condom's protection.

36 Claims, 1 Drawing Sheet

CONDOM DEVICE AND METHOD FOR USING SAME

BACKGROUND OF THE INVENTION

1. Field of the Invention

The present invention relates to condoms used both for birth control and to avoid spread of sexually transmitted diseases. More specifically, it provides a new form of condom which is more effective and reliable than presently known devices, without sacrifice of penile stimulation.

2. Description of the Prior Art

With the recent outbreak of quite serious forms of sexually transmitted diseases, attention again has been focused on condoms both as a highly effective form of birth control and as a proven method of avoiding spread of such diseases. However, because condoms cover the penis, they lessen the sensation experienced during intercourse. This often leads to avoidance of condom use by some and inconsistent use by others. In fact, it is known that the primary cause of failure of condoms as a method of birth control is that they are not properly or consistently used.

To circumvent these problems, various solutions have been employed. The most common solution is to use thinner materials to increase tactile sensation and heat transference. This is only somewhat effective, and it entails a considerable risk. Since a condom's success is completely dependent upon the sheath withstanding the stresses of sexual intercourse, the thinner the material, the less reliable the condom. If a condom tears, its whole purpose is negated. Thinner material also tends to have more stringent handling requirements. For instance, many condomes cannot be exposed to prolonged body heat, such as encountered by storage in a pants' pocket, because their material will denature—increasing the possibility of tearage. Moreover, most such condoms are not durable enough to be used more than once.

In response to these problems, other forms of condoms have been proposed. U.S. Pat. No. 4,323,675 discloses a condom using a harness inside the condom sheath to increase sensation and reliability. U.S. Pat. No. 4,320,752 discloses a semen receptacle to be attached to the end of the penis, collecting the semen while leaving the penis otherwise fully exposed. Neither of these devices is fully satisfactory. The former device appears overly complex and somewhat removed from the natural sensations of intercourse. If this discourages use, it will be ineffective. The latter device, while perhaps increasing sensation, is so minimal in its coverage that it invites seepage both into and out of the penile orifice—again eliminating its effectiveness.

In light of the foregoing, it is a primary object of the present invention to create a condom which provides complete contraceptive and disease barrier protection without loss of the natural sensations of sexual intercourse.

It is a further object of the present invention to provide a durable condom which can be reused and which remains readily available, while being enjoyable enough to use that it will be employed without hesitation.

SUMMARY OF THE INVENTION

The present invention provides a unique condom which is both more effective in protecting against disease and pregnancy, and more sexually stimulating to use.

The invention provides a doubly long flexible tubular sheath with a concentric ring attached midway between its ends. The ring divides the sheath into an open-ended male portion and a closed-ended female portion. When used, the female portion is inserted into the vagina and remains relatively stationary while the male portion attaches to the penis and moves with the penis, through the ring, into and out of the female portion. The result is that the penis is directly stimulated by the interior of the female portion.

Stimulation of the penis can be improved through use of a lubricant, which may include a spermicide for added protection, and texturing on the interior of the female portion. Since the degree of stimulation is not dependent on minimizing the thickness and, consequently, the integrity of the condom sheath, the present invention may be more durably constructed. Accordingly the condom can be used with less care in preventing breakage and may be used more repeatedly than conventional condoms.

The present invention provides a high degree of penile stimulation without compromising the full potential degree of protection available through the use of a condom. This improves the condom's overall effectiveness by encouraging more consistent use.

DETAILED DESCRIPTION OF THE INVENTION

The present invention provides a unique form of condom which maximizes both effectiveness, as a disease barrier and a contraceptive device, and penile sensation.

Figure 1:
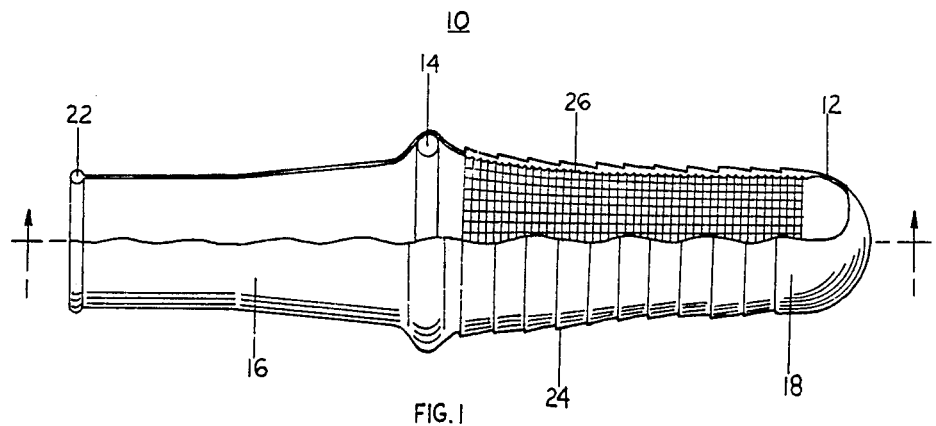
FIG. 1 is an elevational view partially in section of the condom of the present invention, unworn, in its fully extended form.
Figure 2:
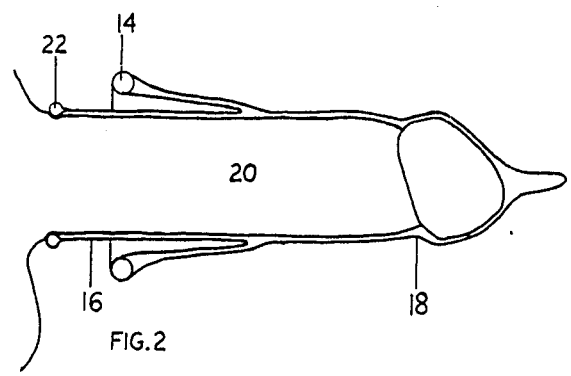
FIG. 2 is a sectional view along line 1—1 of FIG. 1 as the present invention is worn, the penis shown almost fully inserted (ribs and protuberances deleted for clarity).
Figure 3:
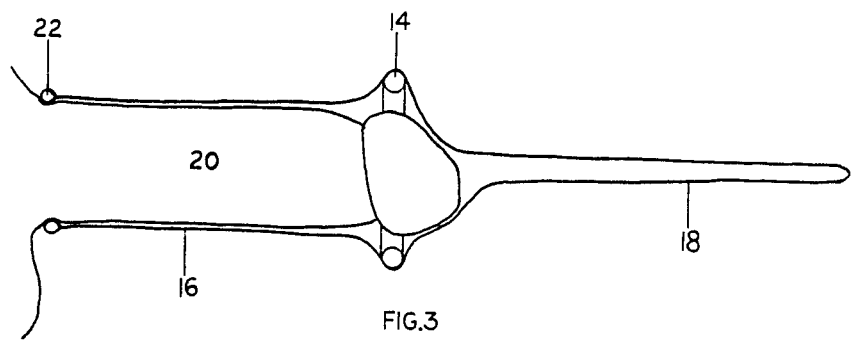
FIG. 3 is the same view as FIG. 2 with the penis shown withdrawn.

As is shown in FIGS. 1, 2, and 3, the condom 10 of the present invention comprises a flexible sheath 12 approximately twice as long as a conventional condom, and a ring 14 attached perpendicular to the longitudinal axis of the sheath 12, approximately midway along its length. The ring 14 should be of sufficient diameter to allow a man's penis to freely pass through it. An inside diameter of 6 to 7 cms. is believed sufficient for most general use. Since the present invention readily lends itself to use without careful individual sizing, it may be manufactured in only a few basic sizes.

The ring 14 effectively divides the condom 10 into two working portions: a male portion 16 and a female portion 18. While gender designations are applied through this disclosure, it should be appreciated that such designations are for descriptive purposes only and are not meant to limit the possible uses of the present invention. Accordingly, the use of the term "sexual intercourse" is applied broadly to include any form of sexual activity which may involve stimulation of a penis.

The purpose of the ring 14 is to assist in maintaining the condom 10 in a functional "centered" position during intercourse, with the male portion 16 and female portion 18 each properly positioned. The invention is believed to function quite adequately using a centering means other than a ring, such as straps, string ties, or other anchoring means attached between the condom and the woman's thighs and/or waist, or through careful selection of materials comprising the condom 10 to help maintain the condom 10 in its fully functional position during intercourse. Although it is not preferred, the present invention may also function without a centering means.

As is shown in FIG. 2, when a penis 20 is fully inserted into the condom 10, the male portion 16 folds around inside the ring 14 and enters the female portion 18. The penis 20 is in full airless contact with the interior of the female portion 18. The female portion 18 should not fit tightly on the penis; stimulation is provided by creating a partial vacuum within the female portion 18, the female portion 18 collapsing against the penis 20 from the pressure of the atmosphere and the vaginal walls. A band 22 of elastic material is molded into the perimeter of the open end of the male portion 16 to hold the condom 10 snugly around the penis 20. This prevents the penis 20 from sliding out of the comdom 10, or semen from seeping out of the condom 10 and body fluid from seeping into the condom 10, during sexual intercourse. Although not preferred, the male portion 16 may be provided with either a bellowed construction so that it folds upon itself without entering the ring 14, or with a sliding seal so that the penis 20 may slide relative to the male portion 16.

The elastic band 22 may be placed at any position along the male portion 16 and may be constructed of any of the materials commonly used to seal condoms around penises. Preferably the band 22 should be placed around the perimeter of the open end of the condom 10, as is commonly done, so to maximize the interior holding capacity of the condom 10 and maximize the distance which the semen must travel between the penile orifice and the sexual partner. An optional elastic loop (not shown) that fits snugly around and behind the man's testes and connects to opposite sides of the band 22 may further inhibit sliding. Similarly, the interior of the male portion 16 may be textured to grip the penis 20 and inhibit slippage.

To use the present invention, the condom 10 is placed on the penis 20 as is shown in FIG. 2. It is desired that all excess air be squeezed out of the condom 10 after placement on the penis 20. The condom-covered penis is then inserted in the conventional manner. During intercourse, the penis 20 may be moved into and out of a woman's vagina in the normal fashion. The entirety of the condom 10, however, does not move with the penis 20.

As is shown in FIG. 3, the female portion 18 remains in the vagina when the penis withdraws. Thus, only the male portion 16, which folds around or upon itself in a smooth rolling and sliding action with its ends held outside the vagina by the ring 14 and the band 22, moves with the penis 20. A smooth, low friction surface finish and/or lubricant on the outside of the male portion 16 may further improve the performance of the condom 10 by preventing binding as it folds.

The advantage of the present invention is that the penis 20 experiences the sensation of direct moving contact against the interior of the female portion 18, which is very similar to the direct contact experienced during unprotected intercourse. Furthermore, as is shown in FIG. 3, the female portion 18 is evacuated and collapses upon withdrawal so the woman continues to experience the sensation of intercourse.

Although it is not necessary, as is shown in FIG. 1, it is beneficial to use exterior texturing, such as ribs 24, to help maintain the female portion 18 relatively stationary during intercourse. The female porton 18 may also be retained in place using easily detachable string ties (not shown) that clip temporarily onto ring 14.

To further improve the sensation experienced by the penis 20, a lubricant (e.g. petroleum jelly, a personal lubricant (e.g. the trademarked product KY-Jelly produced by Johnson and Johnson), or water) may be placed into the condom 10 before the penis 20 is inserted. For contraceptive use, a lubricant containing spermicide, as is commonly employed with contraceptive diaphragms, is preferred. This not only improves the sensation during intercourse, but also provides an additional degree of protection.

It has been found that the penile sensation can be further improved by providing texturing, such as protuberances 26, on the interior of the female portion 18. Such texturing is particularly desired if the condom 10 is constructed out of particularly smooth material, such as latex, and a lubricant is employed. In fact, the sensation experienced using the condom 10 is so exceptional, some may wish to employ it as a marital aid with little regard to either disease protection or birth control.

The sheath 12 may be constructed from any conventional material used for condoms, including flexible plastic, rubber, or animal skin. However, because the stimulation of the penis 20 using the present invention is not dependent upon the penis 20 sensing the vaginal walls, the material may be of a thickness much greater than that normally employed. This assures greater protection against condom failure. It should be noted that because the male portion 16 undergoes considerable folding and unfolding during intercourse, a greater sheath 12 thickness may be necessary to assure against tearage. To this end, it is recommended that a latex rubber be employed of the thickness of at least 0.025 cms. This is approximately five to ten times thicker than conventional condoms. Preferably a surgical quality latex rubber should be used measuring at least 28 to 30 cms. in length and 0.050 to 0.100 cms. in thickness.

The ring 14 may be constructed of any rigid or semi-rigid material or construction, including rubber, hard or soft plastic, wood or metal. It is preferred to construct the ring 14 from a hoop of resilient material, such as a rim of polyurethane or a spring of either plastic or metal, and coating the rim with a layer of latex. If a spring is employed, it may be of any known construction, including a tight coil, or a flat spring. Means of attachment of the ring 14 to the sheath 12 may include permanently gluing it to the sheath's interior or by molding the ring 14 directly into the sheath 12 to make the ring 14 integral with the condom 10.

Figures 4, 5:
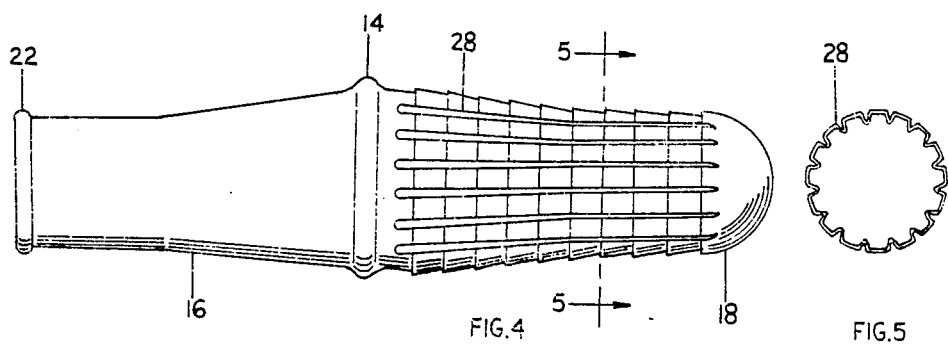
FIG. 4 is an elevational view of another embodiment of the present invention, unworn, in its fully extended form.
FIG. 5 is a sectional view along line 5—5 of FIG. 4.

Passage of the male portion 16 through the ring 14 is facilitated if the male portion 16 is tapered from the ring 14 to approximately half the distance to the open end of the condom 10 and if the female portion 18 is tapered from the ring to approximately half the distance to the closed end of the condom 10. Additionally, it has been found that the operation of the present invention is further improved by constructing the female portion 18 as is shown in FIGS. 4 and 5.

If the walls of the female portion 18 contain convolutions 28, the female portion 18 more readily remains stationary during withdrawal of the penis 20 and it more readily expands to accept the penis 20 and the male portion 16 during insertion. This construction also may improve penile sensation during intercourse.

The present invention produces a condom which provides superior protection against both pregnancy and disease while retaining the natural sensations of sexual intercourse. The present invention can create a condom which may be constructed of either conventional materials of a greater thickness than that commonly employed in condom manufacturing or of more durable unconventional materials. In either case, a condom is created which is far more durable than presently known condoms and which can much better endure repeated use. Moreover, the more durable condom may be more readily kept available since its materials should not have to be as carefully safeguarded against excessive heat or mechanical stress. It is believed that a more enjoyable condom will lead to more frequent and consistent use—greatly diminishing the spread of disease and unwanted pregnancy.

While particular embodiments of the present invention are disclosed herein, it is not intended to limit the invention to such disclosure, and changes and modifications may be incorporated and embodied within the scope of the following claims.

What is claimed is:

1. A condom to be worn by a male during sexual intercourse with a second partner comprising
    a flexible sheath having an interior surface, an exterior surface, an open-ended external to the second partner male portion, a closed-ended female portion and, centering means being provided intermediate the ends of the sheath, separating the male portion and the female portion;
    said male portion having means to attach to a penis and to seal said open end;
    said female portion being bodily inserted up to but not including said centering means and remaining relatively stationary during intercourse; and
    said male portion being adapted to fold, allowing the penis to move into and out of the female portion of said sheath during intercourse.
2. A condom in accordance with claim 1 wherein said centering means is a ring.
3. A condom in accordance with claim 2 wherein said ring is permanently anchored to said sheath.
4. A condom in accordance with claim 3 wherein said ring is integral with said sheath.
5. A condom in accordance with claim 2 wherein said ring comprises semi-rigid material.
6. A condom in accordance with claim 5 wherein said semi-rigid material comprises a circular hoop of resilient material.
7. A condom in accordance with claim 6 wherein said circular hoop of resilient material comprises a rim covered with a coating of latex.
8. A condom in accordance with claim 2 wherein said ring comprises a rigid ring of plastic.
9. A condom in accordance with claim 2 wherein the male portion passes through the ring during intercourse.
10. A condom in accordance with claim 9 wherein the female portion is tapered to more readily accept the male portion.
11. A condom in accordance with claim 9 wherein the male portion is tapered to more readily pass through the ring during intercourse.
12. A condom in accordance with claim 1 wherein said centering means is an anchoring means to attach to a participant during intercourse.
13. A condom in accordance with claim 1 wherein said means to attach the male portion to a penis is a band of elastic material
14. A condom in accordance with claim 13 wherein said band of elastic material is attached to the perimeter of the open end of the male portion.
15. A condom in accordance with claim 13 wherein when said condom is worn its interior is completely enclosed, and wherein the band of elastic material snugly surrounds the penis and prevents fluid communication between the interior and exterior of the condom.
16. A condom in accordance with claim 1 wherein a lubricant is placed in the flexible sheath prior to attaching the condom to the penis.
17. A condom in accordance with claim 16 wherein the lubricant contains a spermicide.
18. A condom in accordance with claim 1 wherein said sheath comprises flexible material at least 0.025 cms. thick.
19. A condom in accordance with claim 13 wherein said flexible material is latex.
20. A condom in accordance with claim 1 wherein the female portion is provided with means to maintain the female portion relatively stationary during intercourse.
21. A condom in accordance with claim 20 wherein said means to maintain the female portion relatively stationary during intercourse includes texturing on the exterior surface of the female portion.
22. A condom in accordance with claim 1 wherein the interior of said female portion is provided with means to increase stimulation of the penis.
23. A condom in accordance with claim 22 wherein the means to increase stimulation of the penis includes texturing of the interior surface of the female portion.
24. A condom in accordance with claim 1 wherein said sheath is sufficiently durable to allow the condom to be used repeatedly without compromising its effectiveness.
25. A condom in accordance with claim 24 wherein said durability is provided by constructing the sheath from latex of at least 0.025 cms. thickness.
26. A condom in accordance with claim 1 wherein the female portion is provided with convolutions.
27. A method of sexual intercourse which avoids mixture of body fluids while maintaining stimulation of a penis comprising
    providing a flexible sheath condom with a centering means attached intermediate its ends separating the sheath into a male portion and a female portion;
    attaching the male portion to the penis;
    inserting the female portion up to but not including said centering means and maintaining said female portion in place during intercourse;
    causing the male portion to fold, allowing the penis to move into and out of the female portion.
28. A method of sexual intercourse in accordance with claim 27 which includes providing a ring as said centering means, and causing the male portion to fold through said ring to allow the penis to move into and out of the female portion.

29. A method of sexual intercourse in accordance with claim 28 which includes providing a lubricant to be inserted into said condom prior to attachment to the penis, which lubricant may include a spermicide.

30. A method of sexual intercourse in accordance with claim 29 wherein the interior of said female portion is provided with texturing to increase stimulation of the penis.

31. A condom to be worn on a penis during sexual intercourse comprising
a tubular flexible sheath having an interior surface, and an exterior surface, said sheath having an open proximal end and a closed end;
said closed end of the sheath being bodily inserted and remaining relatively stationary during intercourse;
said sheath being provided with means to prevent the open proximal end of the sehath from being inserted during intercourse said means includes a ring affixed intermediate the ends of the sheath and an elastic band affixed to said open proximal end of the sheath;
said ring being of sufficient size to prevent its insertion during intercourse;
said elastic band attaching to and creating a fluid-tight seal around the penis;
wherein said penis is moved at least partially into and out of the sheath during intercourse, with a portion of said sheath between said proximal open end and said ring folding around said ring, penile stimulation being provided by contact with the interior of the sheath.

32. A condom in accordance with claim 31 wherein said ring comprises semi-rigid material.

33. A condom in accordance with claim 31 wherein the sheath is provided with means to maintain it relatively stationary during intercourse.

34. A condom in accordance with claim 33 wherein said means to maintain the female portion relatively stationary during intercourse includes texturing on the exterior surface of the sheath.

35. A condom in accordance with claim 34 wherein the interior of said sheath is provided with means to increase the stimulation of the penis.

36. A condom in accordance with claim 31 wherein the sheath is provided with convolutions.

* * * * *

UNITED STATES PATENT AND TRADEMARK OFFICE
CERTIFICATE OF CORRECTION

PATENT NO. : 4,798,600
DATED : January 17, 1989
INVENTOR(S) : Michael E. Meadows It is certified that error appears in the above-identified patent and that said Letters Patent is hereby corrected as shown below:

Col. 1, line 36: "condomes" should be --condoms--

Col. 1, line 43: "Patent No. 4,323,675" should be --Patent No. 4,232,675--

Col. 5, line 16: "manufacturing" should be --manufacture--

Signed and Sealed this

Thirteenth Day of June, 1989

*Attest:*

DONALD J. QUIGG

*Attesting Officer*   Commissioner of Patents and Trademarks